US00PP14413P29

(12) United States Plant Patent
Houbraken

(10) Patent No.: US PP14,413 P2
(45) Date of Patent: Dec. 23, 2003

(54) ARGYRANTHEMUM FRUTESCENS PLANT NAMED 'ARGYRANTIS'

(50) Latin Name: *Argyranthemum frutescens*
Varietal Denomination: Argyrantis

(75) Inventor: Anna M. W. P. Houbraken, Enkhuizen (NL)

(73) Assignee: Syngenta Seeds BV, Enkhuizen (NL)

( * ) Notice: Subject to any disclaimer, the term of this patent is extended or adjusted under 35 U.S.C. 154(b) by 14 days.

(21) Appl. No.: 10/340,260

(22) Filed: Jan. 10, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Bruce Vrana; Edouard G. Lebel

(57) ABSTRACT

A distinct cultivar of Marguerite Daisy plant named 'Argyrantis' characterized by its compact mounding plant habit, good field performance, good-bad weather tolerance, short internodes and short flower stems, freely flowering with numerous inflorescences per plant, pure white ray florets and bright yellow disc florets.

1 Drawing Sheet

Varietal denomination: 'Argyrantis'.

BACKGROUND OF THE NEW PLANT

The present invention relates to a new distinct cultivar of Marguerite Daisy plant, botanically known as *Argyranthemum frutescens* and referred to by the cultivar name 'Argyrantis.' The new cultivar is a product of a planned breeding program conducted by the inventor in Enkhuizen, The Netherlands. The objective of the breeding program was to develop a more vigorous plant that flowers early in the greenhouse and has a good field performance during the whole summer. The plant can be used as a landscaper by its mounding plant habit. As a result of an open pollination of 'Harvest snow' (unpatented variety) the present cultivar was created in 1998 in Enkhuizen. 'Argyrantis' was asexually reproduced by cuttings for 4 years and tested under different conditions in Europe on Syngenta trial ground properties. It has been found to retain its distinctiveness characteristics through successive propagation, and its novelty appears to be firmly fixed.

DESCRIPTION OF THE DRAWING

This new Marguerite Daisy plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Marguerite Daisy plant. The data which defines these characteristics were collected from asexual reproductions carried out in Enkhuizen, Netherlands. The plant history was taken on 25 weeks old plants, grown on the field in Enkhuizen, The Netherlands in full sun with day temperatures ranging from 15 and 30 degrees C., and night temperatures ranging from 5 to 18 degrees C. Color references are primarily to The R.H.S. Color Chart of The Royal Horticultural Society of London.

Differences between the new cultivar 'Argyrantis' and its parent

| | 'Argyrantis' | 'Harvest Snow' |
|---|---|---|
| Plant Height | 28 cm | 20 cm |
| Spreading Area | 55 cm | 50 cm |
| Number of Branches/Plant | 14 | 10 |

The plant:

*Classification — Botanical.*—*Argyanthemum frutescens* cv. 'Argyrantis'.

Parentage:

*Female parent.*—Seedling selection of *Argyanthemum frutescens*, 'Harvest Snow' (not patented). Breeders code of the new plant is B 8-2.

*Male parent.*—Unidentified selection of *Argyanthemum frutescens.*

Propagation:

*Type cuttings.*—Terminal cuttings.

*Time to initiate roots.*—7 to 10 days at air temperature of 21 degrees C.

*Time to develop roots.*—7 to 14 days at air temperature of 18 degrees C.

Plant description:

*Growth habit.*—Mounding and compact.

*Plant height.*—28 cm.

*Spreading area of plant.*—55 cm.

*Strength.*—Resistant to cold and wet weather.

*Branching character.*—Freely branching, plants do not require pinching.

*Crop time.*—About 8–10 weeks are required to produce a finished flowering plant in a 10.5 cm container from a good developed cutting.

The stem:

*Diameter.*—5 cm.

*Shape.*—Round (cylindrical).

*Anthocyan pigmentation.*—Absent.

*Length of internode.*—0.4–0.8 cm.

*Pubescence.*—Absent.

*Color.*—144C.

The foliage:
*Arrangement.*—Alternate.
*Shape of leaf.*—Bipinnatisect.
*Leaf apex.*—Acute.
*Leaf base.*—Attenuate.
*Texture.*—Glabrous smooth.
*Length.*—2–5 cm.
*Width.*—1.3 cm.
*Depth of incision.*—Laciniate.
*Color.*—Upper side: 137A. Lower side: 137B.
*Pubescence.*—No pubescence.
*Petiole.*—Length: Absent.
*Venation.*—Shape: Pinnate. Color: 137C.

The bud:
*Peduncle.*—Length: 6–9 cm. Strength: Strong. Texture: Smooth. Color: 144A.
*Size.*—Diameter: 5 mm. Length: 1 cm.
*Shape.*—Ovoid.
*Color.*—162D.

Inflorescence:
*Diameter.*—3–3.5 cm.
*Form.*—Capitulum with 1 series of ray florets and more series of disc florets.
*Receptacle shape.*—Bit flat.
*Receptacle height.*—4 mm.
*Involucre/phyllaries.*—3 series of 5 bracts, tightly to receptacle. Shape: Elliptic, with broad apex. Margin: Entire. Length: 3 mm. Color: Upper: 144A. Lower: 146A.
*Fragrance.*—None.
*Quantity of inflorescences.*—50–100 flowers per plant depending on growing conditions and age of plant.
*Flowering period.*—April til October.

Ray florets:
*Shape of ray florets.*—Oblong.
*Apex.*—Rounded, little incised.
*Base.*—Cordate.
*Margin.*—Entire.
*Color.*—155D.
*Overlapping of ray florets.*—Yes.
*No. of ray florets per inflor.*—±18.
*Texture.*—Smooth.
*Size of ray floret.*—Length: 1.2–1.5 cm. Width: 4–5 mm.

Disc florets:
*Shape of disc florets.*—Tubular with 5 lobes.
*Disc flowers diameter.*—1 mm.
*Color.*—Yellow.

Androecium:
*Anther color.*—Yellow 5A.
*Pollen color.*—Yellow 5A.
*Amount of pollen.*—Scarce.
*Number of stamens.*—5 in central disc florets only.

Gynoecium:
*Pistil number.*—One per floret (ray florets only).
*Pistil length.*—About 2 mm.
*Syle color.*—Yellow green 144C.
*Style length.*—About 1 mm.
*Stigma color.*—Yellow green 4A.
*Stigma shape.*—Bilobed.
*Ovary color.*—144C.

Disease resistance: No susceptibility nor resistance to fungal, bacterial or viral pathogens has been noted.

Seed: Seed production is not typically observed.

What is claimed is:

1. A new and distinct variety of Argyranthemum plant, substantially as herein illustrated and described, characterized particularly as to novelty by its mounding and vigorous plant habit with good and stable flowering potential through the whole summer under N-W European conditions.

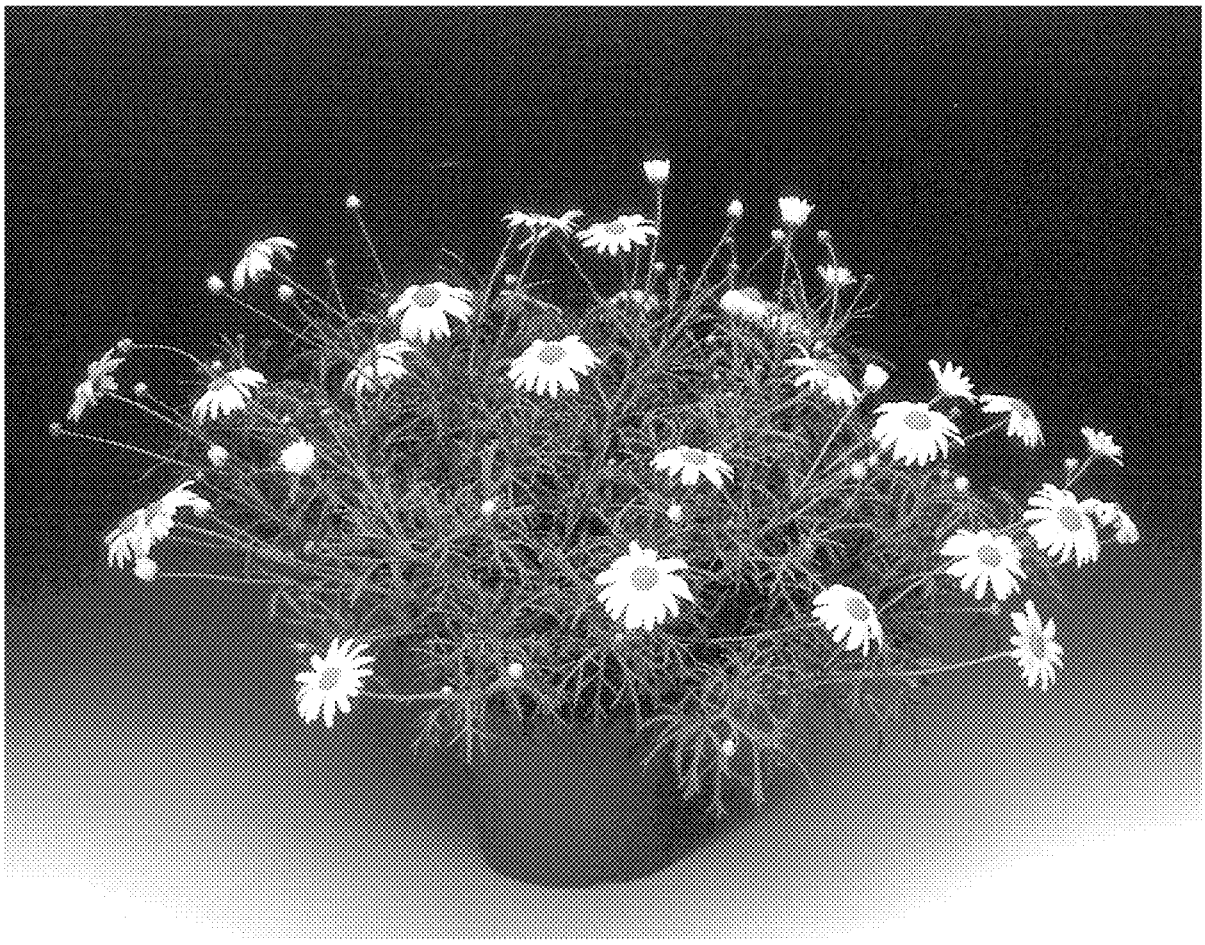

* * * * *